(12) United States Patent
Karapetian

(10) Patent No.: US 11,969,164 B2
(45) Date of Patent: Apr. 30, 2024

(54) CORKSCREW TISSUE ANCHOR

(71) Applicant: Edwards Lifesciences Corporation, Irvine, CA (US)

(72) Inventor: Emil Karapetian, Huntington Beach, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 317 days.

(21) Appl. No.: 17/322,504

(22) Filed: May 17, 2021

(65) Prior Publication Data

US 2021/0267585 A1 Sep. 2, 2021

Related U.S. Application Data

(62) Division of application No. 16/368,650, filed on Mar. 28, 2019, now Pat. No. 11,026,673.

(60) Provisional application No. 62/669,622, filed on May 10, 2018.

(51) Int. Cl.
*A61B 17/04* (2006.01)
*A61F 2/24* (2006.01)
*A61B 90/00* (2016.01)

(52) U.S. Cl.
CPC ........ *A61B 17/0401* (2013.01); *A61F 2/2487* (2013.01); *A61B 2017/0409* (2013.01); *A61B 2017/0416* (2013.01); *A61B 2017/0427* (2013.01); *A61B 2017/0441* (2013.01); *A61B 2017/0445* (2013.01); *A61B 2090/3966* (2016.02); *A61B 2090/3983* (2016.02); *A61F 2220/0016* (2013.01); *A61F 2230/0091* (2013.01); *A61F 2250/0098* (2013.01)

(58) Field of Classification Search
CPC .................. A61B 1/313; A61B 1/3132; A61B 2017/0429; A61B 2017/043; A61B 2017/0435; A61B 2017/0437; A61B 2017/0445; A61B 2017/0427; A61B 2017/0446; A61B 2017/0448; A61B 2017/044; A61B 2017/0441; A61B 2017/0443; A61B 2017/0464; A61B 17/0401

See application file for complete search history.

(56) References Cited

U.S. PATENT DOCUMENTS

| 5,868,789 A | 2/1999 | Huebner |
| 6,108,582 A | 8/2000 | Fischer, Sr. |
| 6,544,273 B1 | 4/2003 | Harari et al. |
| 6,884,248 B2 | 4/2005 | Bolduc et al. |
| 7,149,587 B2 | 12/2006 | Wardle et al. |
| 8,108,054 B2 | 1/2012 | Helland |
| 8,523,755 B2 | 9/2013 | Almog et al. |
| 8,728,097 B1 | 5/2014 | Sugimoto et al. |
| 8,747,462 B2 | 6/2014 | Hill et al. |

(Continued)

FOREIGN PATENT DOCUMENTS

| EP | 0967923 A1 | 1/2000 |
| EP | 2943132 A1 | 11/2015 |

(Continued)

*Primary Examiner* — Wade Miles
(74) *Attorney, Agent, or Firm* — Chang & Hale LLP

(57) ABSTRACT

A tissue anchor includes a driver head associated with a proximal portion of the tissue anchor, a pointed tip portion associated with a distal portion of the tissue anchor, a tissue-engagement portion disposed between the driver head and the pointed tip portion, and a cover configured to cover at least a portion of the tissue-engagement portion.

6 Claims, 8 Drawing Sheets

(56) References Cited

U.S. PATENT DOCUMENTS

| | | |
|---|---|---|
| 9,072,890 B2 | 7/2015 | Friedman et al. |
| 9,693,865 B2 | 7/2017 | Gilmore et al. |
| 2003/0105465 A1 | 6/2003 | Schmieding et al. |
| 2003/0163161 A1 | 8/2003 | Barron et al. |
| 2006/0015006 A1 | 1/2006 | Laurence et al. |
| 2006/0282085 A1 | 12/2006 | Stone et al. |
| 2009/0105816 A1 | 4/2009 | Olsen et al. |
| 2013/0096672 A1 | 4/2013 | Reich et al. |
| 2014/0081323 A1 | 3/2014 | Hawkins |
| 2015/0272586 A1 | 10/2015 | Herman et al. |
| 2018/0049875 A1 | 2/2018 | Iflah et al. |

FOREIGN PATENT DOCUMENTS

| | | |
|---|---|---|
| WO | 2007084411 A2 | 7/2007 |
| WO | 2014117087 A1 | 7/2014 |

CORKSCREW TISSUE ANCHOR

RELATED APPLICATION

This application is a divisional application of co-pending U.S. patent application Ser. No. 16/368,650, filed Mar. 28, 2019, which claims priority based on U.S. Provisional Application No. 62/669,622, filed May 10, 2018, the contents of both of which are incorporated herein by reference in their entireties.

BACKGROUND

Field

The present disclosure generally relates to the field of biological tissue anchors and tissue-piercing devices.

Description of Related Art

Tissue anchors and other devices for piercing and/or embedding in tissue or other material are used for various applications. The shape and/or features of such devices can lead to entanglement and visibility issues.

SUMMARY

In some implementations, the present disclosure relates to a tissue anchor comprising a driver head associated with a proximal portion of the tissue anchor, a pointed tip portion associated with a distal portion of the tissue anchor, a tissue-engagement portion disposed between the driver head and the pointed tip portion, and a cover configured to cover at least a portion of the tissue-engagement portion.

In certain embodiments, the pointed tip portion is disposed within the cover. The cover may comprise cloth and/or polymer film. In some embodiments, the tissue anchor further comprises a swivel feature. For example, the swivel feature may include a suture-holding feature and/or may comprise a fastener configured to fasten to one or more of the cover and target biological tissue. The tissue anchor may further comprise a radiopaque material associated with the cover. In some embodiments, the tissue-engagement portion has a helical form. In some embodiments, the cover is configured to bunch up as the helical tissue-engagement portion passes through the cover and into tissue. The helical tissue-engagement portion may be configured to pass through the cover as the driver head is rotated and pressed against biological tissue. For example, the pointed tip portion may be configured to puncture the cover and at least partially pass therethrough when pressed against the biological tissue. In some embodiments, the tissue-engagement portion comprises one or more barbs and/or a hypodermic tube. In some embodiments, the tissue anchor further comprises a suture that is secured to one or more of the driver head and the helical tissue-engagement portion.

In some implementations, the present disclosure relates to a method for anchoring into biological tissue. The method comprises approximating a tissue anchor to biological tissue, the tissue anchor being at least partially encapsulated in a cover, engaging a driver head portion of the tissue anchor, puncturing at least one of the cover of the tissue anchor and the biological tissue with a pointed tip portion of the tissue anchor and rotating the driver head portion to advance at least a portion of a corkscrew portion of the tissue anchor into the biological tissue.

The method may further comprise providing a catheter containing the tissue anchor, delivering the catheter into a ventricle of a heart associated with the biological tissue, and expelling the tissue anchor from the catheter. For example, the method further comprises carrying another tissue anchor having another cover within the catheter, wherein the cover of the other tissue anchor prevents entanglement of another corkscrew portion of the other tissue anchor with a suture coupled to the tissue anchor. In some embodiments, the method further comprises visually determining that the corkscrew portion of the tissue anchor has advanced into the biological tissue from external to a body associated with the biological tissue. For example, visually determining may involve identifying one or more radiopaque markings associated with the cover using X-ray imaging. In some embodiments, rotating the driver head portion causes the cover to gather between the biological tissue and the driver head.

In some implementations, the present disclosure relates to a system comprising a delivery catheter, a corkscrew tissue anchor having a proximal head portion and a distal pointed portion, a suture coupled to the corkscrew tissue anchor, and a cover covering at least part of the corkscrew tissue anchor. The cover may include one or more visual markers identifiable using radiation imaging. The system may further comprise a swivel fastener coupled to the corkscrew tissue anchor and configured to fasten to the cover.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

DETAILED DESCRIPTION

Figure 1:
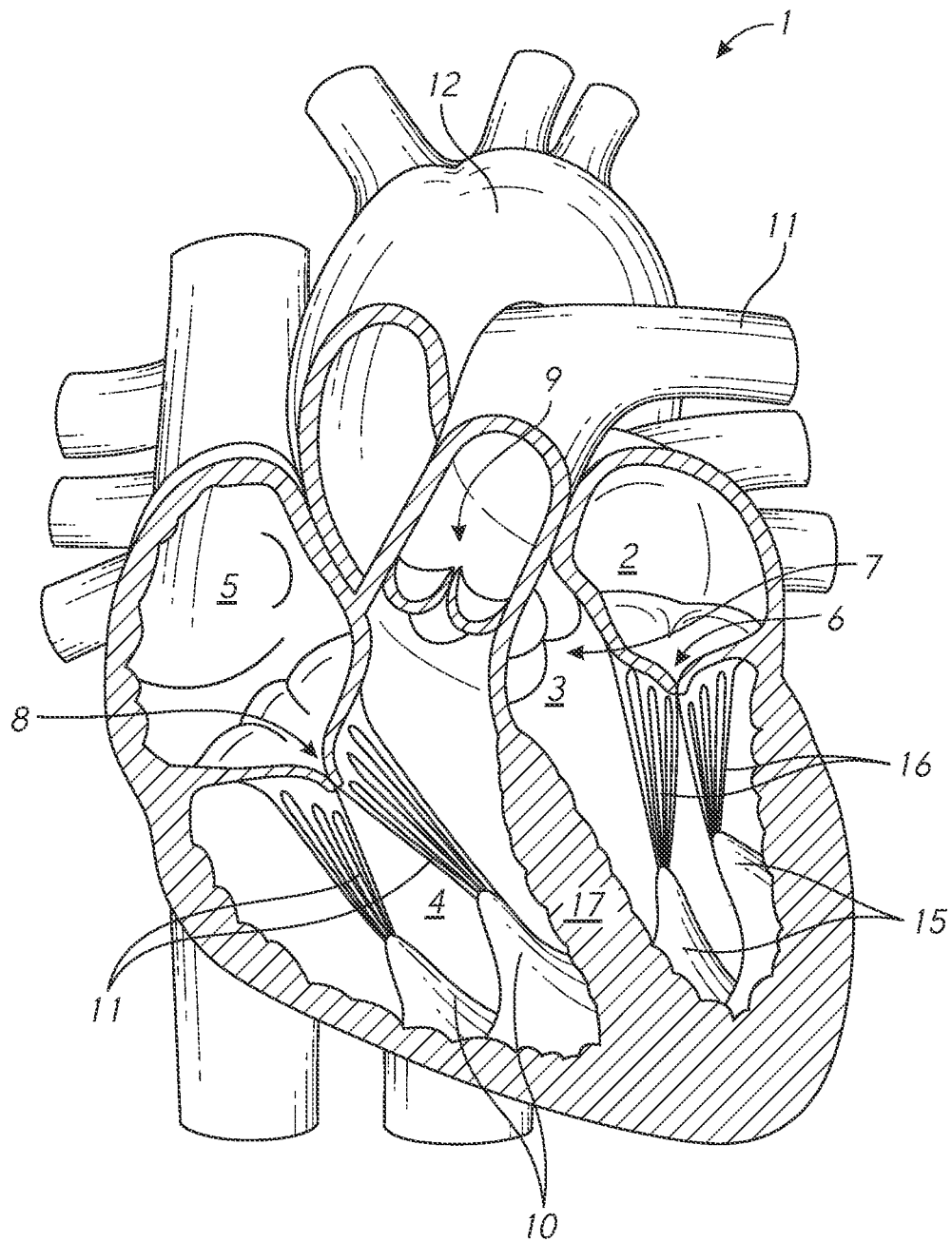
FIG. 1 provides a cross-sectional view of a human heart.

The headings provided herein are for convenience only and do not necessarily affect the scope or meaning of the claimed invention.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Overview

The present disclosure provides systems, devices, and methods relating to entanglement-resistant tissue anchors and other tissue-piercing/penetrating devices, which may be used for certain medical procedures, or for other applications. Certain of the disclosed embodiments further provide tissue anchoring and/or puncturing devices having certain anti-unscrewing or anti-disengagement features associated therewith. Devices disclosed herein may be designed or configured to be embedded in, or otherwise attached, to biological tissue. However, it should be understood that principles disclosed herein may be applicable to devices and methods for embedding or securing to non-biological tissue as well. In some embodiments, the present disclosure relates to corkscrew-type anchors, which are described in detail herein. However, it should be understood that the disclosed principles may be applicable to other types of tissue anchors or tissue-piercing devices (e.g., hypodermic needles or tubes, or the like). Therefore, description herein of corkscrew-type anchors is applicable to other types of anchors and devices, including devices that do not have a corkscrew form or shape.

Corkscrew anchors may be used to attach or anchor into biological tissue. For example, in connection with certain cardiac procedures, tissue anchors or the like may be used to embed in or otherwise secure to cardiac anatomy, which may be useful for various therapies. For example, cardiac resynchronization therapy (CRT), percutaneous angioplasty, or other therapies may utilize one or more corkscrew anchors, or other types of anchors, in some implementations.

Corkscrew and other types of tissue anchors or tissue-puncturing devices, may be used in connection with various medical procedures, including cardiac operations. For convenience, in some contexts, the present disclosure describes embodiments in the context of cardiac operations. However, it should be understood that the disclosed embodiments may be implemented in connection with any type of medical procedure. To provide context for the disclosure herein relating to cardiac operations, FIG. 1 and the associated description show and describe a human heart. In humans and other vertebrate animals, the heart generally comprises a muscular organ having four pumping chambers, wherein the flow thereof is at least partially controlled by various heart valves, namely, the aortic, mitral (or bicuspid), tricuspid, and pulmonary valves. The valves may be configured to open and close in response to a pressure gradient present during various stages of the cardiac cycle (e.g., relaxation and contraction) to at least partially control the flow of blood to a respective region of the heart and/or to blood vessels (e.g., pulmonary, aorta, etc.).

FIG. 1 illustrates an example representation of a heart 1 having various features relevant to certain embodiments of the present inventive disclosure. The heart 1 includes four chambers, namely the left atrium 2, the left ventricle 3, the right ventricle 4, and the right atrium 5. A wall of muscle 17, referred to as the septum, separates the left 2 and right 5 atria and the left 3 and right 4 ventricles. The heart 1 further includes four valves for aiding the circulation of blood therein, including the tricuspid valve 8, which separates the right atrium 5 from the right ventricle 4. Dysfunction of a heart valve may be treated using various procedures that involve anchoring to cardiac tissue, which may be used to provide a tethering force for valve correction. Tissue anchors in accordance with the present disclosure may advantageously provide for tissue anchoring for valve or other cardiac correction procedures with improved visibility and/or anti-entanglement features, as described in detail below. Tissue anchoring for cardiac operations may involve anchoring to the ventricular wall or septum.

The tricuspid valve 8 may generally have three cusps or leaflets and may generally close during ventricular contraction (i.e., systole) and open during ventricular expansion (i.e., diastole). The valves of the heart 1 further include the pulmonary valve 9, which separates the right ventricle 4 from the pulmonary artery 11, and may be configured to open during systole so that blood may be pumped toward the lungs, and close during diastole to prevent blood from leaking back into the heart from the pulmonary artery. The pulmonary valve 9 generally has three cusps/leaflets, wherein each one may have a crescent-type shape. The heart 1 further includes the mitral valve 6, which generally has two cusps/leaflets and separates the left atrium 2 from the left ventricle 3. The mitral valve 6 may generally be configured to open during diastole so that blood in the left atrium 2 can flow into the left ventricle 3, and advantageously close during diastole to prevent blood from leaking back into the left atrium 2. The aortic valve 7 separates the left ventricle 3 from the aorta 12. The aortic valve 7 is configured to open during systole to allow blood leaving the left ventricle 3 to enter the aorta 12, and close during diastole to prevent blood from leaking back into the left ventricle 3.

Heart valves may generally comprise a relatively dense fibrous ring, referred to herein as the annulus, as well as a plurality of leaflets or cusps attached to the annulus. Generally, the size of the leaflets or cusps may be such that when the heart contracts the resulting increased blood pressure produced within the corresponding heart chamber forces the leaflets at least partially open to allow flow from the heart chamber. As the pressure in the heart chamber subsides, the pressure in the subsequent chamber or blood vessel may become dominant and press back against the leaflets. As a result, the leaflets/cusps come in apposition to each other, thereby closing the flow passage.

The atrioventricular (i.e., mitral and tricuspid) heart valves may further comprise a collection of chordae tendineae and papillary muscles for securing the leaflets of the respective valves to promote and/or facilitate proper coaptation of the valve leaflets and prevent prolapse thereof. The papillary muscles, for example, may generally comprise finger-like projections from the ventricle wall. With respect to the tricuspid valve 8, the normal tricuspid valve may comprise three leaflets (two shown in FIG. 1) and three corresponding papillary muscles 10 (two shown in FIG. 1). The leaflets of the tricuspid valve may be referred to as the anterior, posterior and septal leaflets, respectively. The valve leaflets are connected to the papillary muscles by the chordae tendineae 11, which are disposed in the right ventricle 4 along with the papillary muscles 10. Although tricuspid valves are described herein as comprising three leaflets, it should be understood that tricuspid valves may occur with two or four leaflets in certain patients and/or conditions; the principles relating to papillary muscle adjustment disclosed herein are applicable to atrioventricular valves having any number of leaflets and/or papillary muscles associated therewith.

The right ventricular papillary muscles 10 originate in the right ventricle wall, and attach to the anterior, posterior and septal leaflets of the tricuspid valve, respectively, via the chordae tendineae 11. The papillary muscles 10 of the right ventricle 4 may have variable anatomy; the anterior papillary may generally be the most prominent of the papillary muscles. The papillary muscles 10 may serve to secure the leaflets of the tricuspid valve 8 to prevent prolapsing of the leaflets into the right atrium 5 during ventricular systole. Tricuspid regurgitation can be the result of papillary dysfunction or chordae rupture.

With respect to the mitral valve 6, a normal mitral valve may comprise two leaflets (anterior and posterior) and two corresponding papillary muscles 15. The papillary muscles 15 originate in the left ventricle wall and project into the left ventricle 3. Generally, the anterior leaflet may cover approximately two-thirds of the valve annulus. Although the anterior leaflet covers a greater portion of the annulus, the posterior leaflet may comprise a larger surface area in certain anatomies.

The valve leaflets of the mitral valve 6 may be prevented from prolapsing into the left atrium 2 by the action of the chordae tendineae 16 tendons connecting the valve leaflets to the papillary muscles 15. The relatively inelastic chordae tendineae 16 are attached at one end to the papillary muscles 15 and at the other to the valve leaflets; chordae tendineae from each of the papillary muscles 15 are attached to a respective leaflet of the mitral valve 6. Thus, when the left ventricle 3 contracts, the intraventricular pressure forces the valve to close, while the chordae tendineae 16 keep the leaflets coapting together and prevent the valve from opening in the wrong direction, thereby preventing blood to flow back to the left atrium 2. The various chords of the chordae tendineae may have different thicknesses, wherein relatively thinner chords are attached to the free leaflet margin, while relatively thicker chords (e.g., strut chords) are attached farther away from the free margin.

Although certain embodiments are described herein in the context of cardiac operations, it should be understood that such description is applicable to other types of biological tissue and/or procedures, as well as certain non-biological applications.

Corkscrew Anchors

Figure 2:
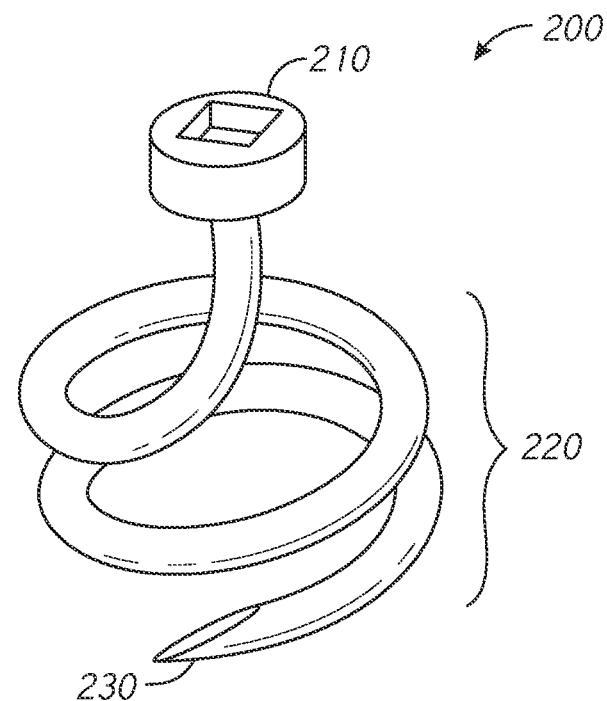
FIG. 2 provides a perspective view of a tissue anchor in accordance with one or more embodiments.

FIG. 2 illustrates a perspective view of a corkscrew tissue anchor 200 in accordance with one or more embodiments. The corkscrew anchor 200 comprises a helical portion 220 that terminates in a tissue-penetrating/piercing tip portion 230, which may advantageously be pointed in shape. The corkscrew anchor 200 may further comprise a driver head portion 210, which may be shaped or dimensioned to be engaged by a driver tool of some kind in order to allow for exertion of rotational force on the tissue anchor 200. Generally, when the pointed tip 230 is placed against biological tissue or other material, rotation of the tissue anchor 200 (e.g., clockwise rotation with respect to the illustrated embodiment) may cause the helical portion 220 of tissue anchor 200 to be screwed into the tissue or material, and thereby become at least partially embedded therein. For example, with respect to a cardiac operation, the helical portion 220 may be embedded into the endocardium and/or myocardium layer(s) of the heart.

Figure 3:
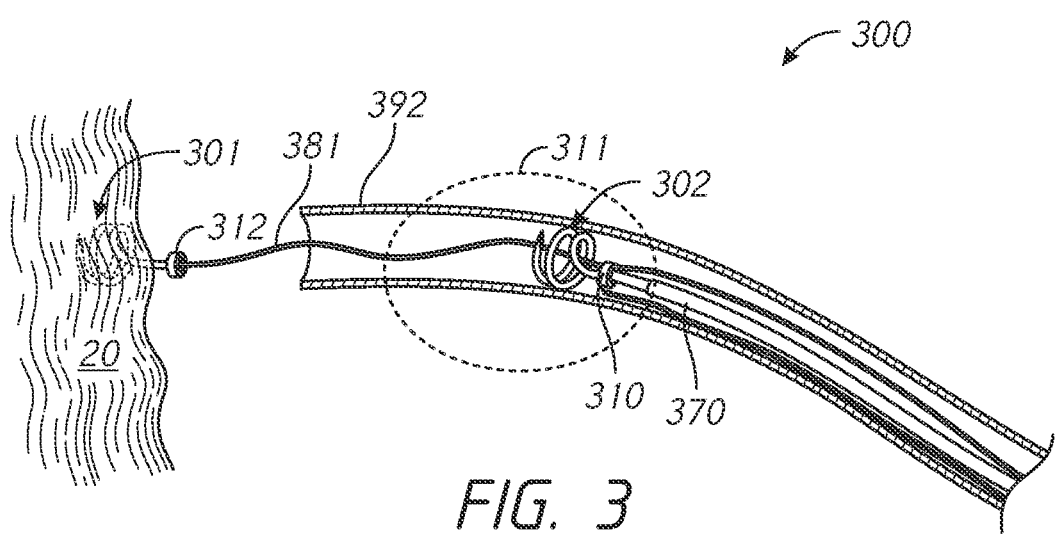
FIG. 3 illustrates a delivery system for one or more tissue anchors in accordance with one or more embodiments.

Corkscrew anchors and/or other types of tissue anchors may be used to treat structural heart disease, such as heart valve dysfunction, ventricular dilation, and/or the like. Generally, tissue anchors, such as corkscrew anchors, may be delivered to a target operational site using a delivery catheter or system. FIG. 3 illustrates an example delivery system 300 for delivering one or more tissue anchors (301, 302) to a target site. For example, one or more tissue anchors may be delivered to a target site for the purpose of embedding the tissue anchor(s) into local biological tissue 20, such as the ventricular wall of the heart, or other biological tissue. One or more of the anchors 301, 302, may be coupled to a tethering suture (e.g., 381), which may be used to tether certain biological anatomy as part of a medical procedure. The delivery system 300 further comprises one or more driver tools or components 370, which may be configured to engage with a driver head 310 of the tissue anchor 302, to thereby exert force, such as rotational force, thereon to cause the respective anchor to pierce or embed into the target tissue.

Where a single delivery catheter 392 is used to transport a plurality of tissue anchors and/or sutures, as shown, the geometry or form of a corkscrew anchor 302 may lead to entanglements with the suture 381 associated with other tissue anchor 301 or device within the catheter 392. The suture 381 may be considered a cinching suture for the tissue anchor 301. In addition, the geometry or form of the corkscrew anchor (e.g., 301 or 302) may result in entanglement with certain other anatomical features external to the catheter 392, such as chordae tendineae, trabeculae carneae, or the like with respect to ventricular procedures in a heart. In addition to issues relating to entanglement of corkscrew anchors, and/or other types of tissue anchors or devices, anchor unscrewing or other disengagement may result, particularly under tethering tension that the embedded tissue anchor may be subjected to after implantation thereof. In addition, with respect to medical procedures in which the target operational site is visually obscured with respect to the operating physician, visual assessment that a tissue anchor is properly engaged with the target tissue may be difficult, particularly where fluoroscopy or other imaging technology is relied upon for visibility.

As referenced above, corkscrew anchors can be used in various surgical procedures to attach and/or anchor into biological tissue. For example, with respect to certain cardiac procedures, corkscrew anchors can be used to puncture and/or anchor into the cardiac anatomy. Example procedures that may involve corkscrew anchoring can include anchoring of cardiac resynchronization therapy (CRT) leads, annuloplasty device anchoring, among others. Corkscrew anchors utilized in medical procedures may be coupled to a suture or other structure, and may serve to anchor thereto. With respect to therapies used to treat structural heart disease, use of corkscrew tissue anchors may present certain advantages and disadvantages. For example, use of corkscrew anchors having traditional configurations can lead to entanglement of the corkscrew with a tethering suture or wire. The corkscrew geometry can cause undesirable entanglement, which may occur at least partly within a delivery catheter, or in a heart ventricle, such as entanglement with the chordae tendineae. Suture entanglement in the delivery catheter may be a particular risk where multiple anchors are placed using a single catheter, as shown in the diagram of FIG. 3.

The present disclosure provides tissue anchoring/piercing devices and/or methods that at least partially resolve one or more of the various issues described above with respect to certain tissue anchoring/piercing devices. In some embodiments, the present disclosure provides a tissue anchor or piercing device that is associated with a cover feature, which may comprise cloth, polymer film, or the like, wherein such cover at least partially prevents entanglements of the tissue anchor with sutures and/or biological anatomy. Although certain embodiments are described herein in the context of tissue anchor devices, it should be understood that the principles disclosed herein are applicable to other types of tissue-piercing devices, such as hypodermic needles/tubes. The cover of the tissue anchor may be configured and/or designed such that, as the tissue anchor is rotated or otherwise pushed into the target tissue, the anchor tip pierces the cover, allowing the anchor to pass therethrough. In some embodiments, a cover for a tissue anchor comprises one or more radiopaque markers. In certain embodiments, the cover is made of radiopaque material, such that the cover is substantially entirely radiopaque. Where radiopaque material is used in connection with the cover, as the anchor is pushed out of the cover when embedding in tissue, the radiopaque marker(s) may move with respect to the anchor and/or anchor tip. For example, with respect to a corkscrew anchor, as the corkscrew anchor is twisted into the target tissue, the cover may bunch up outside of the target tissue, and therefore the radiopaque features associated therewith may be viewable relative to the anchor embedded in the tissue, thereby providing a visual indication that at least a portion of the anchor has passed through the cover and embedded in tissue.

In some embodiments, a corkscrew tissue anchor device in accordance with embodiments of the present disclosure comprises a swivel feature, which may at least partially prevent twisting of the suture associated with the anchor during deployment of the anchor. For example, the swivel feature may comprise an engaging fastener pin or spike feature configured to lock into the cover and/or target tissue to at least partially prevent the backing out or unscrewing of the tissue anchor. Furthermore, as the corkscrew anchor is twisted into the target tissue, the cover (e.g., cloth and/or film) may bunch-up, which may serve to create friction to further help prevent the backing-out or unscrewing of the tissue anchor.

Tissue Anchors with Anti-Entanglement and/or Enhanced Visibility Features

Figure 4:
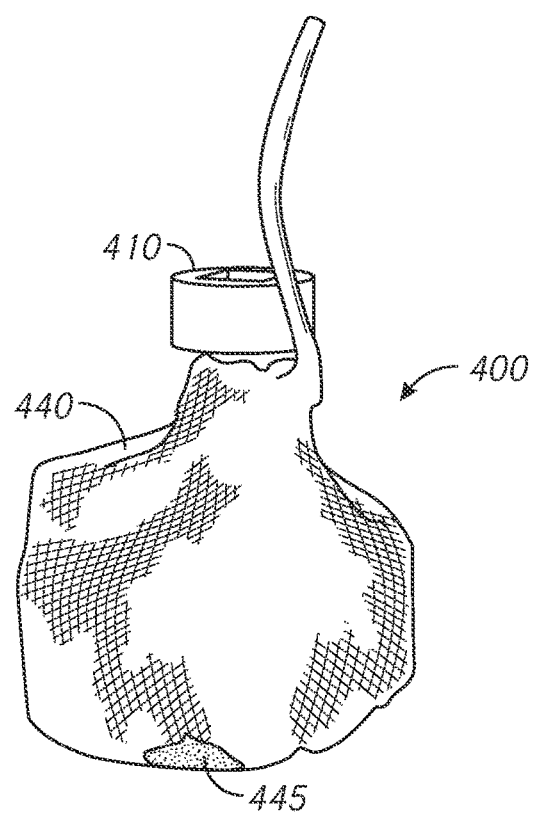
FIG. 4 illustrates a tissue anchor having a cover in accordance with one or more embodiments.
Figure 5:
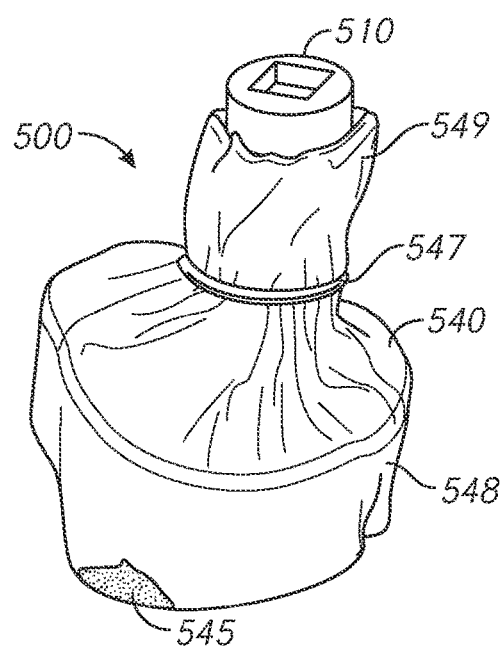
FIG. 5 illustrates a tissue anchor having a cover in accordance with one or more embodiments.
Figure 6:
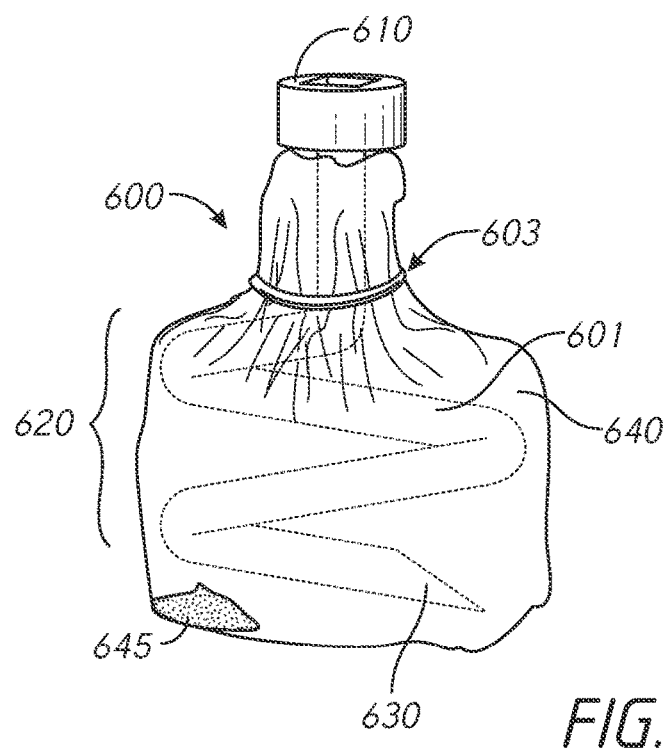
FIG. 6 illustrates a tissue anchor having a cover in accordance with one or more embodiments.

FIGS. 4-6 illustrate embodiments of corkscrew tissue anchors having cover features associated therewith accordance with one or more embodiments. The tissue anchor devices of FIGS. 4-6 may comprise certain anti-entanglement, anti-unscrewing, and/or visibility-enhancement features (e.g. features allowing for improved visibility under fluoroscopy), as referenced above. As described above, corkscrew anchors can be used to attach and/or anchor into cardiac anatomy for various therapies (e.g., CRT lead placement, percutaneous annuloplasty anchoring, etc.).

As referenced above, certain advantages and/or disadvantages may be associated with the use of corkscrew-type anchors in therapies used to treat, for example, structural heart disease. For example, entanglement of corkscrew anchors with sutures and/or biological anatomy (e.g., ventricular anatomy of a heart) can undesirably interfere with the execution of a medical procedure and/or result in physical damage or other harm. Generally, the helical geometry of corkscrew anchors may facilitate or make possible the entangling of the anchor with a suture, wire, chordae tendineae, or the like. As shown in the embodiments of FIGS. 4-6, in certain embodiments, solutions of the present disclosure provide a corkscrew anchor that is covered with a cloth or film, such as a polymer film or the like, which may serve to at least partially prevent or reduce the risk of entanglement with other devices or anatomy.

With respect to FIG. 4, the anchor device 400 comprises a cloth cover 440, which may provide a sock-like covering that at least partially prevents or reduces the risk of the internal corkscrew anchor geometry (not shown) from becoming entangled with sutures or local anatomy at a target operation site, such as chordae tendineae of a heart ventricle, or the like. The diagrams of FIGS. 4 and 5 show tissue anchor devices having different types of covers. For example, with respect to FIG. 4, the cover 440 may comprise a relatively loosely-woven mesh or fabric, whereas the cover 540 of the device 500 of FIG. 5 may comprise a more tightly-woven fabric, or a polymer film or the like. The covers shown in the illustrated embodiments may serve to prevent the corkscrew geometry from entanglement and may allow for the internally-disposed corkscrew anchor to be screwed through, or otherwise penetrate, the distal portion (not shown) of the cover to allow the tissue anchor to embed into the target tissue when approximated thereto. The embodiments of FIGS. 4 and 5 further show radiopaque markers 445, 545 associated with the respective covers of the anchor devices. Although the illustrated embodiments show relatively small radiopaque marker areas, it should be understood that radiopaque or other visibility features associated with a cover of a tissue anchor in accordance with the present disclosure may have any suitable size, shape, or configuration. Furthermore, in some embodiments, at least part of the cover of a tissue anchor comprises radiopaque fabric. For example, in some embodiments, the cover is entirely comprised of radiopaque fabric or material. Generally, radiopaque fabric or material associated with a tissue anchor cover in accordance with the present disclosure may comprise a full circumferential coverage. Furthermore, radiopaque markers for tissue anchor covers may generally be associated at least with a distal portion or end of the tissue anchor device. Radiopaque material may be used with tissue anchor covers in accordance with the present disclosure in order to assist in visualization of placement of the tissue anchor under fluoroscopy. In some embodiments, a cover of a tissue anchor in accordance with the present disclosure comprises fully radiopaque fabric or cloth, wherein the radiopaque characteristic of the cover may allow for visualization of the cover separate from the anchor, which may provide information indicating where the cloth is relative to the tissue anchor and to what extent the tissue anchor is embedded in the target tissue.

FIG. 6 illustrates a side view of a corkscrew tissue anchor device 600 having a cover 640 in accordance with one or more embodiments. In certain embodiments, the cover 640 is configured or designed to cover substantially all of a helical portion 620 of an inner corkscrew form 601 of the anchor device 600. The anchor device 600 includes a driver head 610, which may be manipulated to cause the helical portion of the anchor to rotate, thereby embedding the pointed tip 630 of the anchor into target biological tissue. In certain embodiments, as the corkscrew anchor driver head 610 and/or inner helical portion 620 is wound or rotated and approximated to the target biological tissue, the distal pointed end 630 of the inner corkscrew 601 may be caused to puncture and push through the distal end portion of the cover 640, such that the corkscrew passes out of the cover 640 as it enters the target tissue. In some embodiments, the cover 640 comprises relatively loosely-woven mesh or fabric, such that the pointed tip 630 may pass between the fibers of the mesh or fabric.

The cover 640 of the anchor device 600 comprises one or more radiopaque marker features or portions 645. The radiopaque feature(s) of the cover 640 may advantageously have radiopacity/radiodensity characteristics that provide opacity to the radio wave and/or X-ray portions of the electromagnetic spectrum. It should be understood that the radiopaque feature(s) (e.g., marker 645) may be configured to inhibit the passage of any desired wavelength/frequency of electromagnetic radiation, such that an imaging technique utilizing a particular frequency/wavelength of radiation that is blocked by the radiopaque feature(s) may be used to visualize or identify such features. For example, in a radiograph, the radiopaque feature(s) may have a relatively light appearance, providing visual distinction from surrounding matter. The radiopaque features of embodiments disclosed herein may comprise any type of material, such as one or more of platinum, iridium, barium, iodine, titanium, tungsten, barium sulfate, bismuth compounds, zirconium oxide, or other material or radiopacifier with relatively high electron density contrast. For polymer covers, radiopacifier materials like those listed above may be provided as a filler material according to any suitable or desirable density or loading (e.g., 0-20%, 20-30%, 30-40%, 40-50%, 50-60%, or other density). The density of radiopacifier filler in a polymer cover may advantageously be low enough as to not undesirably affect or degrade the polymer's tensile strength.

The radiopaque marker(s) may show the relative anchor positioning with respect to the cover 640 under fluoroscopy or other imaging mechanism. For example, the radiopaque marking 645 and/or portion of the cover 640 may be positioned and/or configured to move relative to the helical portion 620 of the corkscrew anchor 601 when the tip 630 and at least part of the helical portion 620 are engaged with, and twisted into, tissue or other material. For example, as the anchor 600 is wound, such that the corkscrew anchor 601 pierces and/or passes through the distal end of the cover 640, the cover 640 may become at least partially bunched-up, or drawn proximally/upward, relative to the pointed tip 630 with respect to the orientation illustrated in FIG. 6. Therefore, the relative positioning of the marker portion(s) may change with respect to one or more other features (e.g. metallic features) of the anchor 600. In some embodiments, bunching up of the cover may be caused or facilitated at least in part by an attachment or tightening of the cover 640 at a cinch point 603, which may be generally associated with or proximal end portion of the anchor 600. The collar of the cover 640 may be cinched with a strap, band, tie, suture, or the like. In some embodiments, as shown, the cover 640 may be cinched or otherwise attached at or near a proximal driver head feature 610.

Figure 7:
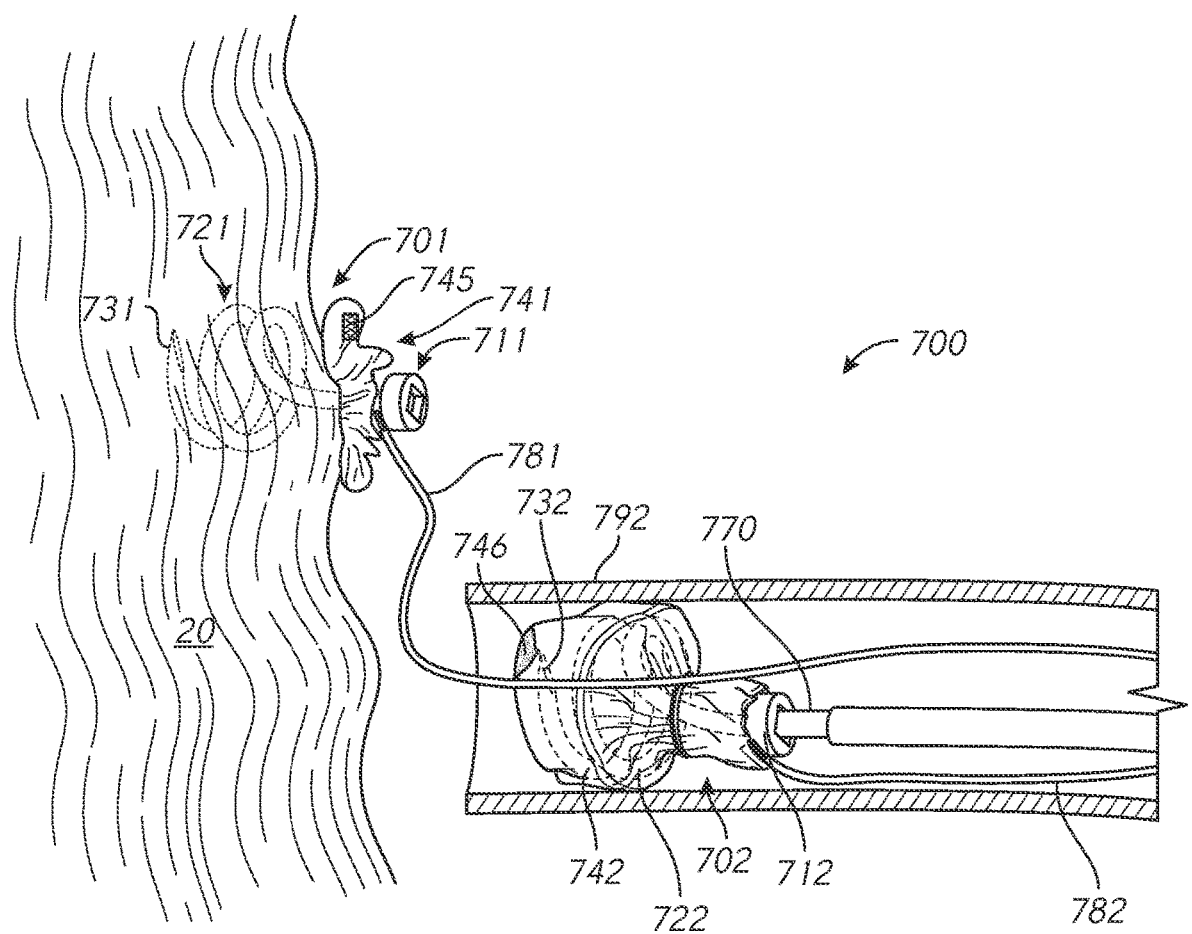
FIG. 7 illustrates a delivery system for one or more tissue anchors in accordance with one or more embodiments.

FIG. 7 illustrates a delivery system 700 for one or more tissue anchors in accordance with one or more embodiments. As shown, in some systems, a plurality of tissue anchors may be delivered to a target site, such as within a ventricle heart, using a single delivery catheter 792. Where such anchors are corkscrew-type anchors, as described in detail above, sutures and/or other components associated with the tissue anchors may become entangled with the corkscrew features of the tissue anchors within the catheter 792 and/or external to the catheter. As shown, in some embodiments, a tissue anchor 702 delivered using a delivery catheter 792 comprises a cover 742 that prevents the corkscrew portion 722 of the tissue anchor 702, which is disposed at least partially within the cover 742, from becoming entangled with, for example, a suture 781, which may be attached to or otherwise associated with another tissue anchor 701. When a tissue anchor (e.g., tissue anchor 701) having a cover feature in accordance with embodiments of the present disclosure is deployed from the delivery catheter 792, the internal corkscrew anchor 721 may be approximated to the surface of the target biological tissue 20 and pushed through the cover 741. For example, as described above, rotating or otherwise embedding the tip 731 of the tissue anchor 701 into the tissue 20 may cause the tip 731 to pass through the cover 741 and enter the tissue 20. While the pointed tip 731 and/or body 721 of the tissue anchor 701 may embed in the tissue 20, the cover 741 may remain generally external to the tissue, as shown, and may become at least partially bunched-up on the surface of the tissue due to the decreased distance between the attachment point of the cover with the anchor, or other surface or feature of the tissue anchor, and the surface of the tissue 20. For example, at least a portion of the cover 741 may become pinned or bunched between the driver head 711 or other feature of the tissue anchor 701 and the surface of the tissue 20.

In addition to preventing entanglement with sutures and other components within the delivery catheter, the cover features (741, 742) may further protect sharp points (e.g. 731, 732) of the tissue anchor(s) and/or other features of the tissue anchor(s) from undesirably catching on local anatomy, or components or devices of the implant system, when the tip of the respective anchor does not properly engage with the target tissue. Therefore, the cover at least partially protects the associated anchor from embolizing or getting entangled in chordae tendineae or other anatomy. For example, where a technician or physician is attempting to twist the tissue anchor 701 into the tissue 20, the cover 741 may protect the internal corkscrew features of the anchor 701 from becoming entangled with local anatomy prior to proper engagement of the anchor with the target tissue.

As shown with respect to the tissue anchor 701, once the anchor passes through the cover 741 and engages with the tissue 20, the cover 741 can collect together or bunch-up. Therefore, where one or more radiopaque markers for marker portions are associated with the cover 741, such marker(s) may experience relative movement with the cover 741 away from the tip 731 and/or helical portion 721 of the anchor 701 generally in the proximal direction. The relative movement of the marker(s) and the other portions of the anchor 701 may be visible under fluoroscopy or other imaging technology. For example, at least a portion of the corkscrew 721 and/or tip 731 may comprise metal or other material that is visible under fluoroscopy.

Figure 8:
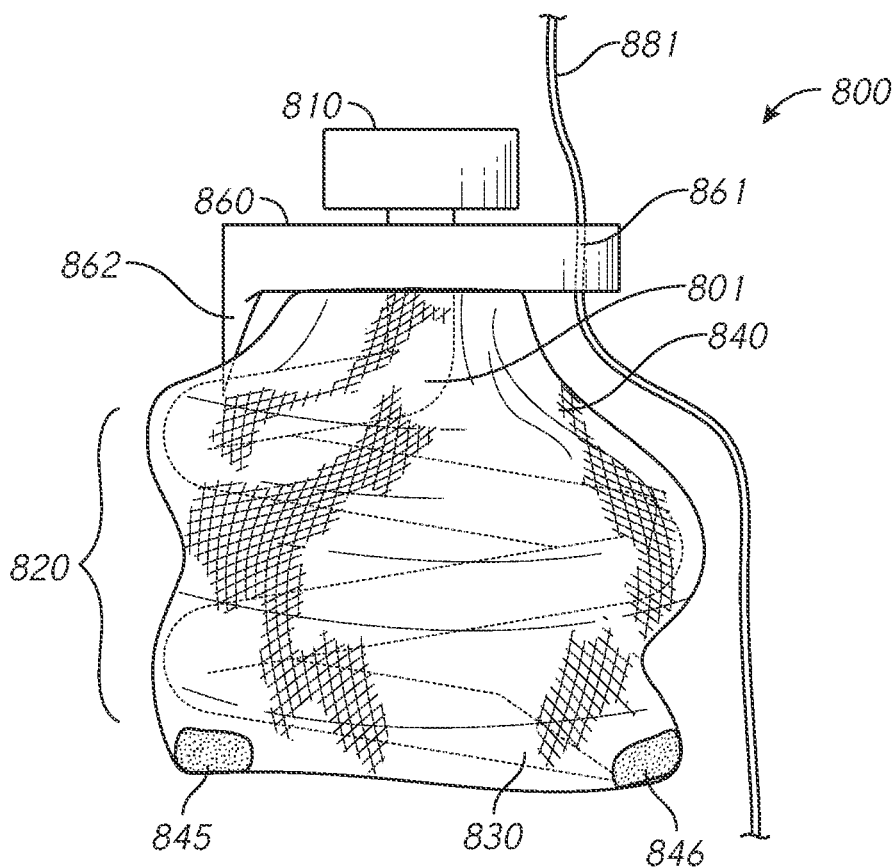
FIG. 8 illustrates a tissue anchor having a cover and a swivel feature in accordance with one or more embodiments.

FIG. 8 illustrates a tissue anchor 800 having a cover 840 covering at least a portion of a corkscrew anchor 801, and a suture-holding swivel feature 860 in accordance with one or more embodiments. The tissue anchor 800 comprises a corkscrew or helical portion 820 which may be at least initially disposed at least partially within the cover 840, as shown. The tissue anchor 800 further comprises a torque driver coupling head feature 810, which may be used to drive the tissue anchor into target biological tissue, such as by twisting or torqueing the driver head 810. The cover 840 may comprise any type of cloth/fabric or film. The cover 840 may be associated with one or more radiopaque markers or marker portions. The marker(s) may be positioned and/or designed to move relative to the corkscrew portion 820 when the corkscrew portion 820 is rotated into target biological tissue. In some embodiments, the entire cloth or cover 840, or at least a substantial portion thereof, is woven of radiopaque fabric/suture. In some embodiments, the cover 840 comprises one or more sewn-on platinum iridium markers, or other types of radiopaque features or markers.

The tissue anchor 800 may further be associated with a suture 881. The suture 881 may be configured to connect to the anchor 800, and may be used to connect the anchor 800 to one or more additional anchors, devices, or anatomical features in connection with a surgical procedure. The tissue anchor 800 comprises a swivel feature 860, which may be configured and/or designed to at least partially prevent suture entanglement during the application of torque to, or rotation of, the corkscrew anchor 820 and/or driver head 810. That is, the swivel feature 860 may at least partially prevent twisting of the suture 881 during deployment of the tissue anchor 800. In some embodiments, the swivel feature 860 is coupled to the suture 881, such that the suture 881 may remain substantially stationary relative to the tissue-engagement portion 820 as the tissue-engagement portion 820 of the tissue anchor 800 is wound into the target tissue. For example, the swivel feature 860 may comprise an aperture or other attachment or securement mechanism 861 configured and/or dimensioned to hold the suture 881. For example, the suture 881 may be slidably held within the aperture or attachment feature 861, such that the suture 881 may be drawn vertically with respect to the orientation of FIG. 8 through the swivel feature 861, as necessary or desired.

In some embodiments, the swivel feature 860 may comprise an engagement fastener 862, such as a pin or spike feature, which may be shaped and configured to embed into the cover 840 and/or biological tissue to help prevent backing-out or unscrewing of the helical tissue-engagement portion 820 of the anchor 800. The swivel feature 860 may at least partially prevent entanglement of the suture 881 during torque application or twisting of the driver head 810, wherein the spike feature 862 may be configured to engage with the cover 840 and/or target biological tissue to prevent unscrewing. As described above, as the helical portion 820 of the anchor is twisted into the target tissue, the cover 840 may collect or become bunched-up between the driver head 810 (or other attachment or contact point between the cover 840 and the internal anchor 801) and the surface of the target tissue. The bunched-up cover 840, when the tissue-engagement portion 820 is penetrated into the target tissue, may create frictional force between the anchor 800 and the surface of the target tissue to help prevent backing-out or unscrewing of the tissue-engagement portion 820 of the anchor.

In some implementations, a delivery system used to deliver the anchor 800 comprises one or more holder features configured and designed to hold the swivel feature 860 with respect to the driver head 810. The driver head 810 may advantageously be allowed to turn, wherein the swivel feature 860 is substantially free relative to the driver head 810, such that rotation of the driver head does not result in a corresponding rotation in the swivel feature 860. Such relative independence of the swivel feature 860 and the driver head 810 may help to keep the suture 881 from becoming entangled as the driver head is rotated.

When the tissue anchor 800 is embedded in the target tissue, the spike feature 862 may pierce and/or otherwise engage with the target tissue as the driver head 810 is approximated to the tissue surface. The spike feature 862 may help to keep the helical portion 820 of the corkscrew anchor 801 from unscrewing, and may be further assisted in preventing disengagement or unscrewing of the tissue anchor by the cover 840, which may be collected between the driver head 810 and/or swivel feature 860 and the tissue surface. That is, although the swivel feature 860 may generally be free to rotate independently of the corkscrew anchor 801 and/or driver head 810, when the spike feature 862 is embedded in the target tissue, the swivel feature 860 may thereby further secure the tissue anchor in the implanted/embedded position.

Figure 9:
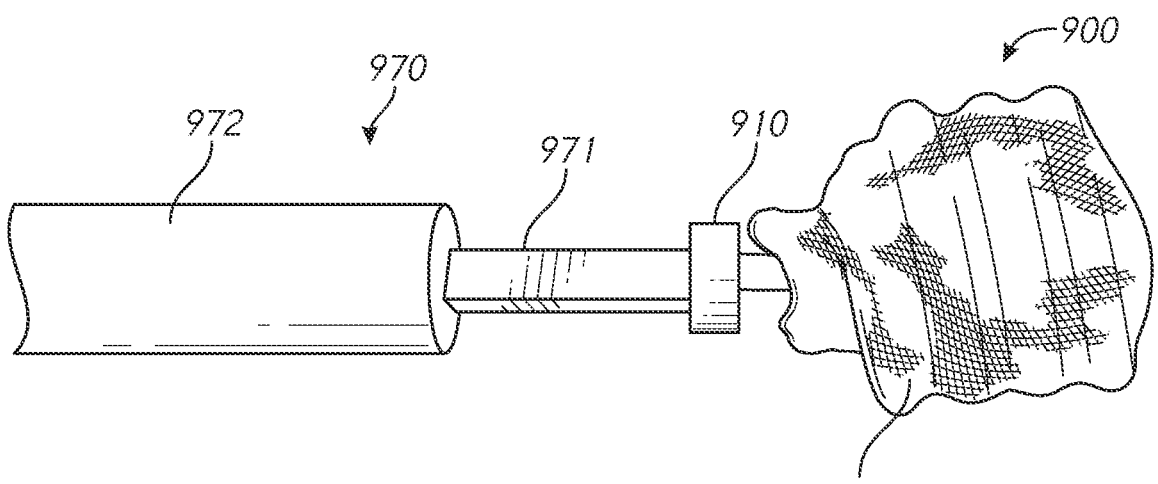
FIG. 9 illustrates a torque driver engaged with a tissue anchor in accordance with one or more embodiments.

FIG. 9 illustrates a side view of a tissue anchor 900 in accordance with embodiments of the present disclosure that is coupled to a torque driver 970. The torque driver 970 is engaged with a driver head 910 of the tissue anchor device 900. The torque driver coupling head 910 may be engaged by the torque driver 970, wherein rotation of the torque driver 970 may thereby be translated to rotation of driver head 910 and anchor 900. The tissue anchor 900 may comprise a cover 940 having disposed or contained therein a tissue-embedding anchor, such as a corkscrew-type anchor or the like.

Additional Tissue-Penetrating Devices and Anchors

Figure 10:
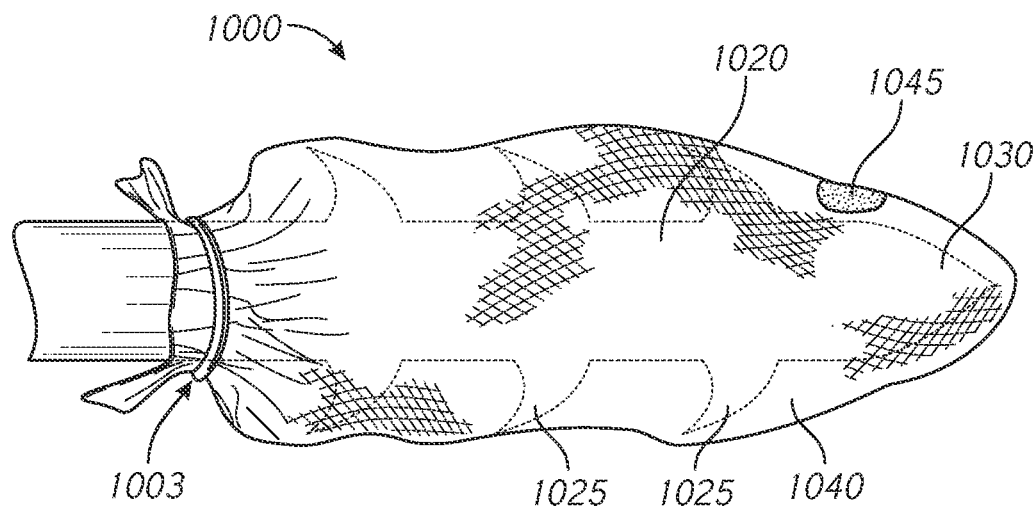
FIG. 10 illustrates a tissue anchor having a cover in accordance with one or more embodiments.

FIG. 10 illustrates a side view of a tissue anchor device 1000 in accordance with one or more embodiments. The tissue anchor device 1000 includes a tissue-engagement portion 1020 having a pointed distal portion 1030, and one or more barbs or other anchoring features 1025. The anchor device 1000 further comprises a cover 1040, which may be similar in certain respects to embodiments of tissue anchor covers described above. The cover may comprise cloth, fabric, polymer film or braid, or any other type of material designed to cover tissue engagement/anchoring features of the tissue anchor device 1000 to prevent entanglement or contact therewith directly by anatomical or device components. The cover 1040 may advantageously be loose enough about the tissue-engagement portion 1020 to allow for the tissue-engagement portion 1020 (e.g. beginning at the pointed distal end 1030) to pierce and/or pass through the distal portion of the cover 1040 when the tissue anchor device 1000 is pressed against target tissue to embed the tissue engagement portion 1020 therein. The cover 1040 may comprise one or more radiopaque markers or marker portions 1045, which may be similar in certain respects to radiopaque materials and markings/features described in detail herein. At least a portion of the cover 1040 may comprise radiopaque material, fabric, polymer, or the like.

Figure 11:
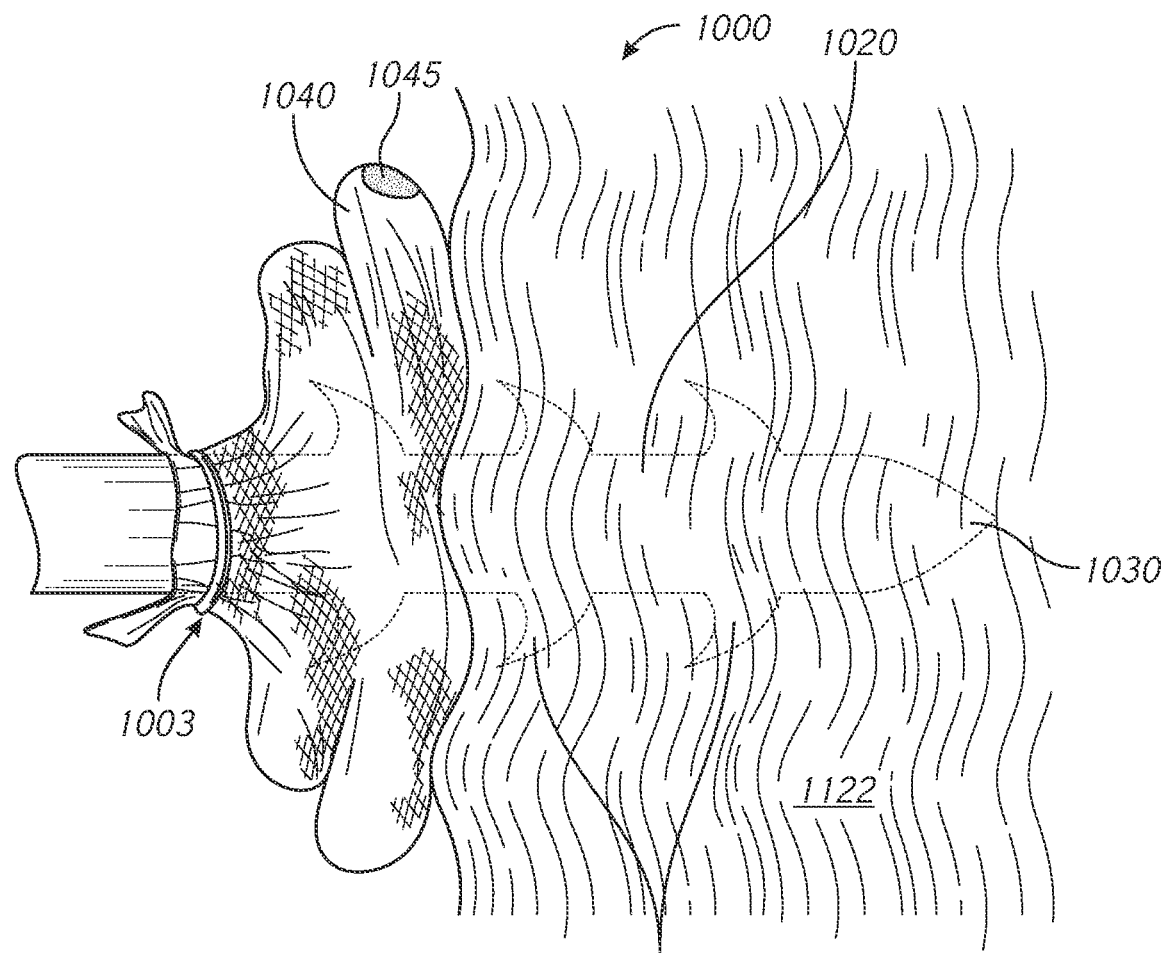
FIG. 11 illustrates a tissue anchor embedded in tissue in accordance with one or more embodiments.

FIG. 11 illustrates the barbed tissue anchor 1000 of FIG. 10 implanted in biological tissue 1122 in accordance with one or more embodiments. As the tissue engagement portion 1020, which is disposed initially internal to the cover 1040, is pressed into the target biological tissue, the tissue engagement portion 1020 may pierce the distal portion of the cover 1040 and pass therethrough into the tissue 1122. However, similarly to embodiments described above, the cover 1040 may not be allowed or inclined to pass into the biological tissue 1122, and may rather collect or bunch-up external to the biological tissue 1122 between the surface of the tissue and a point of attachment of the cover 1040 to the proximal portion of the tissue anchor device 1000, or between the surface of the tissue and a surface or feature of the tissue anchor 1000 at least partly opposite-facing with respect to the tissue surface. Where the cover 1040 comprises one or more radiopaque markers, or other portions of radiopaque material (e.g. the cover 1040 may comprise or consist of radiopaque fabric), such radiopaque feature(s) may advantageously allow for visibility of the relative motion of the cover 1040 to the tissue engagement portion 1020, which may thereby provide an indication of the extent to which the tissue engagement portion 1020 is embedded into the target tissue 1122.

Figure 12:
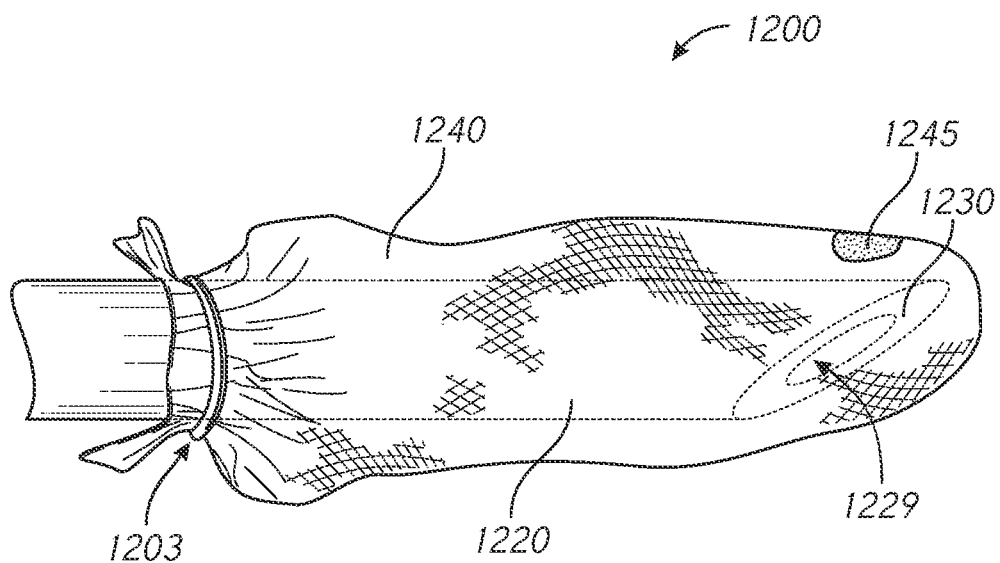
FIG. 12 illustrates a tissue-piercing device having a cover in accordance with one or more embodiments.

FIG. 12 illustrates a side view of a tissue-penetrating device 1200 in accordance with one or more embodiments. The device 1200 comprises a tissue-engagement or penetrating portion 1220, which may comprise a pointed distal portion 1230 configured to pierce target biological tissue, and further comprises a cover 1240 configured to at least partially enclose the tissue-engagement portion 1220 prior to embedding thereof in the target biological tissue. In some embodiments, the tissue-engagement portion 1220 comprises a hypodermic needle or tube, forming an internal lumen 1229, which may be used to introduce certain fluids or materials into the target tissue according to a medical operation or procedure. The lumen 1229 may terminate in a discharge orifice, as shown, for discharging fluid or other material into the target tissue.

The cover 1240 may comprise cloth, fabric, polymer film or braid, or any other type of material designed to cover the tissue-engagement features of the tissue anchor device 1200 to at least partly prevent entanglements or contact therewith directly by anatomical or device components. The cover 1240 may advantageously be loose enough about the tissue engagement portion 1220 to allow for the tissue engagement portion 1220 (e.g. beginning at the point at the distal end 1230) to pierce and/or pass through the distal portion of the cover 1240 when the tissue anchor device 1200 is pressed against target tissue to embed the tissue engagement portion 1220 therein. The cover 1240 may comprise one or more radiopaque markers are marker portions 1245, which may be similar in certain respects to radiopaque materials and markings described in detail herein. At least a portion of the cover 1240 may comprise radiopaque material, fabric, polymer, or the like.

Figure 13:
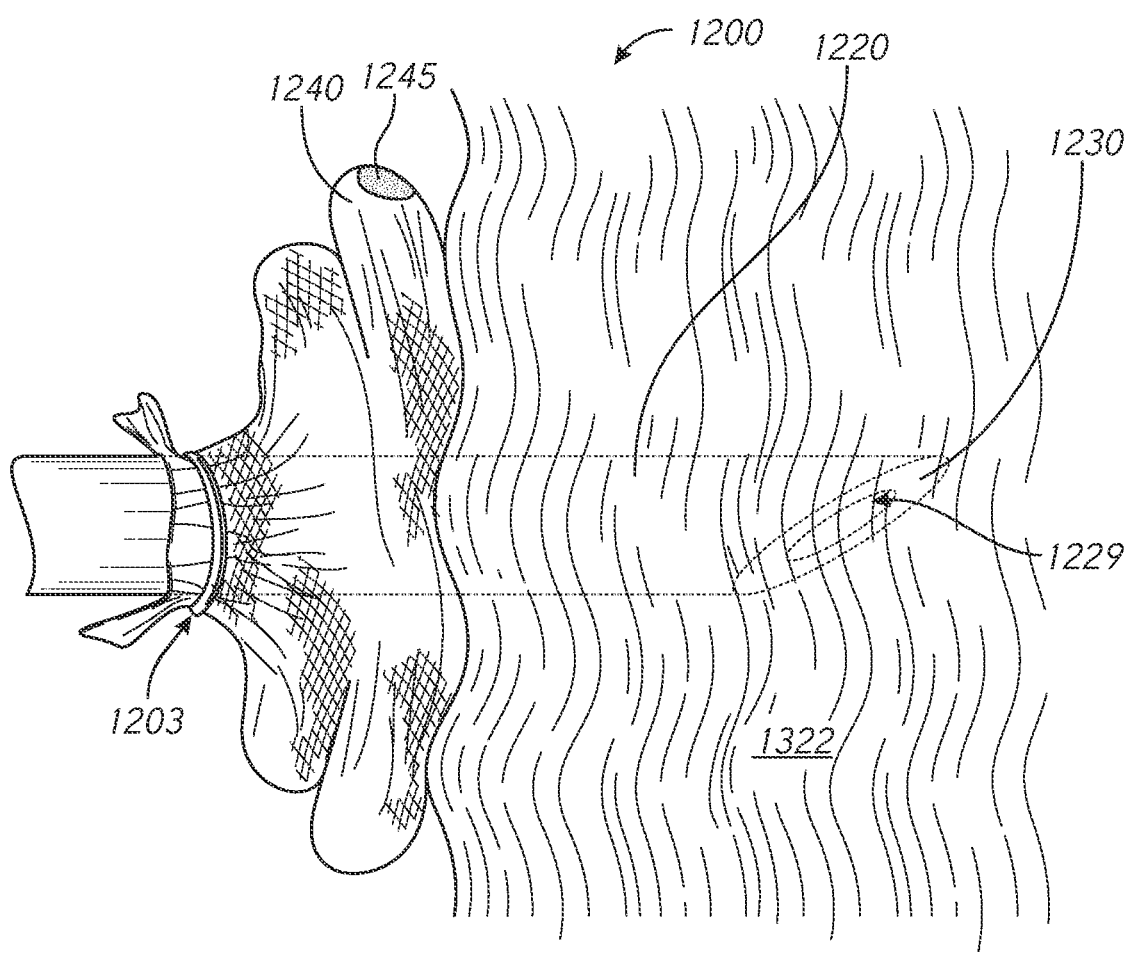
FIG. 13 illustrates a tissue-piercing device embedded in tissue in accordance with one or more embodiments.

FIG. 13 illustrates the tissue-penetrating device 1200 of FIG. 12 embedded in biological tissue 1322 in accordance with more embodiments. As the tissue-engagement portion 1220, which is disposed initially internal to the cover 1240, is pressed into the target biological tissue, the tissue-engagement portion 1220 may pierce the distal portion of the cover 1240 and pass therethrough into the tissue 1322. However, similarly to embodiments described above, the cover 1240 may not be allowed or inclined to pass into the biological tissue 1322, and may rather collect or bunch-up external to the biological tissue 1322 between the surface of the tissue and a point of attachment of the cover 1240 to the proximal portion of the tissue-penetrating device 1200, and/or between the surface or feature of the tissue and a surface of the tissue-penetrating device 1200 that is at least partly opposite-facing with respect to the tissue surface. Where the cover 1240 comprises one or more radiopaque markers, or other portions of radiopaque material (e.g. the cover 1240 may comprise or consist of radiopaque fabric), such radiopaque feature(s) may advantageously allow for visibility of the relative displacement or movement of the cover 1240 to the tissue-engagement portion 1220, which may thereby provide an indication of the extent to which the tissue engagement portion 1220 is embedded into the target tissue 1322.

Tissue-Anchoring/Penetrating Processes

Figure 14:
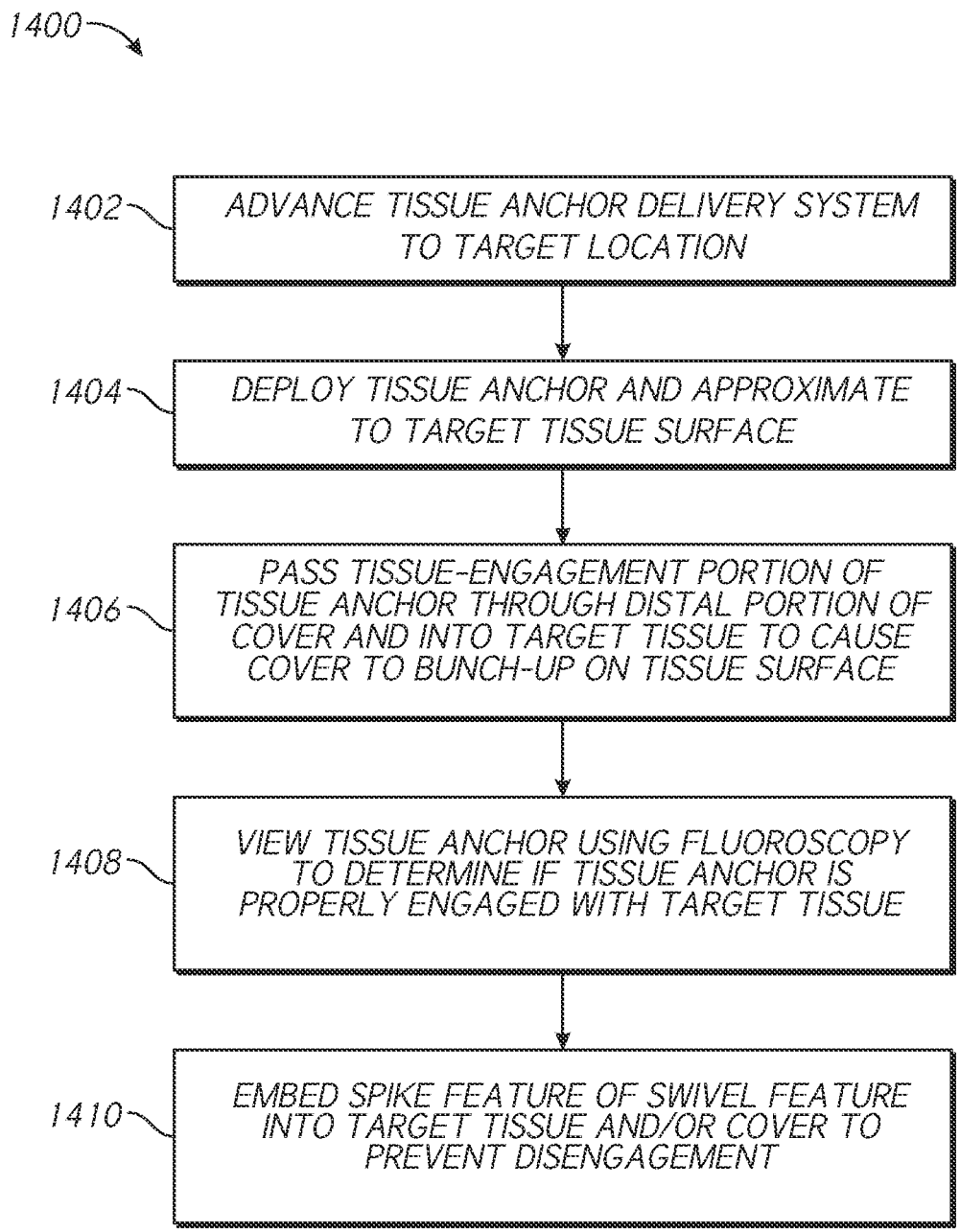
FIG. 14 is a flow diagram illustrating a process for placing a tissue anchor in accordance with one or more embodiments.

FIG. 14 is a flow diagram illustrating a process 1400 for anchoring to or penetrating or embedding in biological tissue or other material in accordance with one or more embodiments. With respect to transcatheter and/or surgical operations, the process 1400 may advantageously result in reduced entanglement risk of anchor or tissue-penetrating devices within the delivery catheter and/or improved visibility of tissue engagement using fluoroscopy, as described in detail herein.

At block 1402, the process 1400 involves advancing a delivery system for one or more tissue anchors to a target location. The one or more tissue anchors may advantageously comprise respective covers, as described in detail herein. For example, in some embodiments the one or more tissue anchors comprises a corkscrew anchor having a cloth or film covering to prevent entanglement. At block 1404, the process 1400 involves deploying a tissue anchor from the delivery system and approximating a tissue anchor to a target tissue surface.

The cover may be configured to bunch-up as an inner corkscrew anchor is twisted. At block 1406, the process 1400 involves passing the tissue-engagement portion of the tissue anchor through a distal portion of the cover and into the target tissue, thereby causing the cover to collect and/or bunch-up on the surface of the target tissue. The cover may comprise a cloth covering for a tissue-engagement portion of the tissue anchor, and may further have one or more radiopaque markers for visibility of the anchor engaging with tissue, as described above.

At block 1408, the process 1400 involves utilizing fluoroscopy (e.g., X-ray) or other imaging technology to view the tissue engagement portion of the tissue anchor device and one or more radiopaque markers or portions of the tissue anchor device to determine that the tissue engagement portion of the tissue anchor device has properly engaged or embedded into the target tissue.

At block 1410, the process 1400 involves embedding a spike feature of a swivel feature of the tissue anchor device into the target tissue and/or cover to thereby secure the tissue engagement portion in the embedded position within the target tissue and prevent disengagement. For example, the tissue anchor may advantageously comprise a swivel feature on a corkscrew anchor that prevents suture entanglement.

Although FIG. 14 and the accompanying description describe tissue anchors, it should be understood that the steps of the process 1400 may relate to other types of tissue-penetrating devices, and description of tissue anchors should be considered to apply to other tissue-penetrating devices as well, such as hypodermic needles and tubes. In addition, although certain devices and processes are disclosed herein context of anchoring to biological tissue, it should be understood that devices and processes disclosed herein are applicable for anchoring into other types of materials, including nonbiological materials.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It will be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A method for anchoring into biological tissue, said method comprising:
    approximating a tissue anchor to biological tissue, the tissue anchor being at least partially encapsulated in a cover that is cinched around a neck portion of the tissue anchor;
    engaging a driver head portion of the tissue anchor;
    puncturing the cover with a pointed tip portion of the tissue anchor; and
    rotating the driver head portion to advance at least a portion of a corkscrew portion of the tissue anchor into the biological tissue.

2. The method of claim 1, further comprising:
    providing a catheter containing the tissue anchor;
    delivering the catheter into a ventricle of a heart associated with the biological tissue; and
    expelling the tissue anchor from the catheter.

3. The method of claim 2, further comprising carrying another tissue anchor having another cover within the catheter, wherein the cover of the other tissue anchor prevents entanglement of another corkscrew portion of the other tissue anchor with a suture coupled to the tissue anchor.

4. The method of claim 1, further comprising visually determining that the corkscrew portion of the tissue anchor has advanced into the biological tissue from external to a body associated with the biological tissue.

5. The method of claim 4, wherein said visually determining involves identifying one or more radiopaque markings associated with the cover using X-ray imaging.

6. The method of claim 1, wherein said rotating the driver head portion causes the cover to gather between the biological tissue and the driver head.

* * * * *